(12) United States Patent
Yoo

(10) Patent No.: US 11,260,202 B2
(45) Date of Patent: Mar. 1, 2022

(54) APPARATUS FOR OSCILLATING, JETTING, AND INJECTING LIPOLYSIS COMPOSITION

(71) Applicant: Seung Min Yoo, Seoul (KR)

(72) Inventor: Seung Min Yoo, Seoul (KR)

( * ) Notice: Subject to any disclaimer, the term of this patent is extended or adjusted under 35 U.S.C. 154(b) by 244 days.

(21) Appl. No.: 16/414,035

(22) Filed: May 16, 2019

(65) Prior Publication Data

US 2020/0238050 A1 Jul. 30, 2020

(30) Foreign Application Priority Data

Jan. 24, 2019 (KR) .......................... 10-2019-0009154

(51) Int. Cl.
*A61M 25/00* (2006.01)
*A61M 5/142* (2006.01)

(52) U.S. Cl.
CPC .......... *A61M 25/007* (2013.01); *A61M 5/142* (2013.01); *A61M 2202/08* (2013.01); *A61M 2205/3344* (2013.01)

(58) Field of Classification Search
CPC .......... A61M 25/0067; A61M 25/0068; A61M 5/00; A61M 5/14; A61M 5/158; A61M 2202/00; A61M 2205/33; A61M 2205/3331; A61M 5/48; A61M 5/32; A61M 2202/08; A61M 2205/3344; A61M 25/007; A61M 5/142; A61M 5/482; A61M 5/484

See application file for complete search history.

(56) References Cited

U.S. PATENT DOCUMENTS

| | | | |
|---|---|---|---|
| 2008/0319417 A1 | 12/2008 | Quijano et al. | |
| 2013/0165860 A1* | 6/2013 | Doud | A61M 39/0247 604/117 |
| 2020/0054824 A1* | 2/2020 | Hagarty | A61M 1/79 |
| 2020/0276395 A1* | 9/2020 | Zyman | A61M 5/3291 |

FOREIGN PATENT DOCUMENTS

| | | | | |
|---|---|---|---|---|
| KR | 2013-0060684 A | 6/2013 | | |
| KR | 2018-0039514 A | 4/2018 | | |
| WO | WO-2007/059005 A2 | 5/2007 | | |
| WO | WO-2009/099988 A2 | 8/2009 | | |
| WO | WO-2009099988 A2 * | 8/2009 | ............... | A61P 3/04 |
| WO | WO-2020/051200 A1 | 3/2020 | | |

OTHER PUBLICATIONS

Extended European Search Report for European Patent Application No. 20187458.3, Sep. 16, 2020, (6 pages), European Patent Office, Munich, Germany.

* cited by examiner

*Primary Examiner* — Jason E Flick
(74) *Attorney, Agent, or Firm* — Alston & Bird LLP

(57) ABSTRACT

Provided is an apparatus for injecting a lipolysis composition, the apparatus including a lipolysis composition storage, a pump, and at least one nozzle-type needle.

11 Claims, 5 Drawing Sheets

APPARATUS FOR OSCILLATING, JETTING, AND INJECTING LIPOLYSIS COMPOSITION

CROSS-REFERENCE TO RELATED APPLICATION(S)

This application claims the benefit of Korean Patent Application No. 10-2019-0009154 filed on Jan. 24, 2019, in the Korean Intellectual Property Office, the disclosure of which is incorporated herein by reference.

BACKGROUND

1. Field of the Invention

One or more example embodiments relate to an apparatus for oscillating, jetting, and injecting a lipolysis composition.

2. Description of the Related Art

Since a demand for a body contouring market is huge and continues to grow every year, various liposuction and lipolysis methods are being developed.

Considering disadvantages faced by liposuction in the past, in a field of weight control and body contouring, manufacturers have shifted their focus from traditional liposuction to a minimal invasiveness and even non-invasiveness, and are developing lipolysis methods in accordance therewith. However, even if an anesthetic is added to an injection, there is still serious side effects such as inflammation and pain at an injection site after an anesthesia is worn off. In some cases, there are postoperative pain, nerve palsy, local necrosis, or risk of infection, which may limit a use of the anesthetic.

Accordingly, it is a trend of a market to develop a local lipolysis injection apparatus that effectively maximizes a local lipolysis effect with less side effects and overcomes the mentioned disadvantages and limitation in response to a high consumer demand for a safer product.

SUMMARY

An aspect provides, to solve the foregoing issues, a lipolysis composition injection apparatus that minimizes repulsion of a patient toward pain and adverse effects such as skin depression, skin deflection, and wrinkling, which may occur due to failure in evenly removing fat of a wide area, and evenly removes fat of a wide area to prevent or minimize the adverse effects.

However, the problems to be solved in the present disclosure are not limited to the foregoing problems, and other problems not mentioned herein would be clearly understood by one of ordinary skill in the art from the following description.

According to an aspect, there is provided an apparatus for injecting a lipolysis composition, the apparatus including a lipolysis composition storage, a pump, and at least one nozzle-type needle.

The pump may be configured to periodically supply the lipolysis composition to the nozzle-type needle.

The lipolysis composition may be jetted at a high pressure into a subcutaneous fat layer through the nozzle-type needle.

A periodical high-pressure jet of the lipolysis composition may be performed on a subcutaneous fat layer through the nozzle-type needle in response to a periodical supply of the pump.

An oscillation may be applied to the subcutaneous fat layer through the periodical high-pressure jet.

The oscillation may be a repetitive oscillation of 10 hertz (Hz) to 1000 Hz.

The high-pressure jet may be performed at a pressure of 50 pounds per square inch (psi) to 1000 psi.

The lipolysis composition may be supplied at a volume of 300 milliliters per minute (ml/min).

The nozzle-type needle may include four to eight nozzle-type needles.

The nozzle-type needle may be positioned at an interval of 10 centimeters (cm) to 20 cm and inserted into the subcutaneous fat layer.

The nozzle-type needle may include a horizontal jet hole at an end.

A longitudinal end of the nozzle-type needle may be blocked.

A jet of the lipolysis composition performed through the horizontal jet hole of the nozzle-type needle may include a radial spraying jet.

The nozzle-type needle may be four or more needles and provided at an interval of 10 cm to 20 cm to penetrate a flexible patch plate, and a length by which the nozzle-type needle penetrates the flexible patch plate may be adjustable in a range of 1 cm to 5 cm.

EFFECT

According to example embodiments, a lipolysis composition injection apparatus may effectively inject a lipolysis composition between a skin layer and a subcutaneous layer, minimize impact or stimulation of subcutaneous fat, and maximize a lipolysis effect. In addition, it is possible to perform a stable and efficient lipolysis treatment with increased accuracy. Also, it is possible to minimize repulsion of a patient toward pain and adverse effects such as skin depression, skin deflection, and wrinkling which may occur due to failure in evenly removing fat of a wide area or adverse effects such as pain, bruising, erythema, edema, hardening, and itching after the treatment, and maximize the lipolysis effect at a local site.

DETAILED DESCRIPTION

Figure 1:
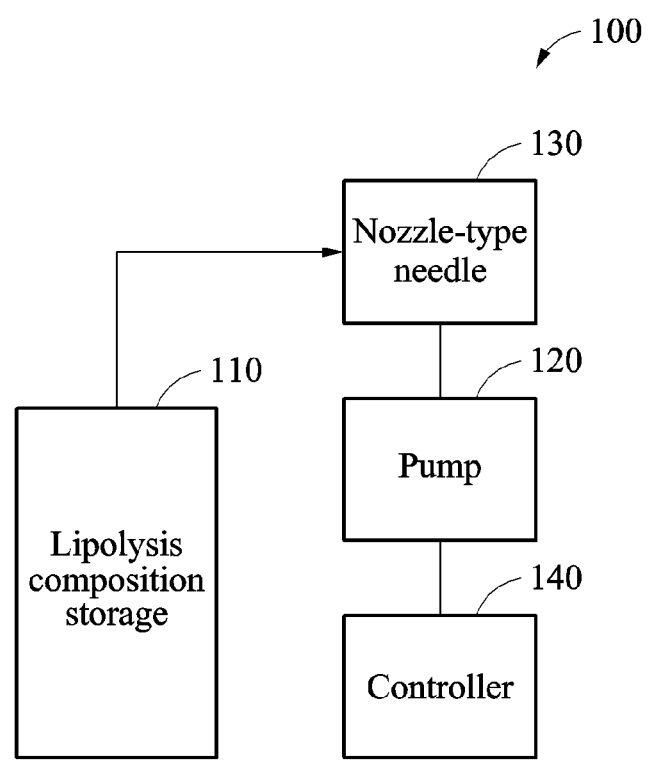
FIG. 1 is a diagram illustrating an apparatus for injecting a lipolysis composition according to an example embodiment.

Hereinafter, example embodiments of the present disclosure will be described in detail with reference to the accompanying drawings. When it is determined detailed description related to a related known function or configuration they may make the purpose of the present disclosure unnecessarily ambiguous in describing the present disclosure, the detailed description will be omitted here. Also, terminologies used herein are defined to appropriately describe the example embodiments and thus may be changed depending on a user, the intent of an operator, or a custom of a field to which the present disclosure pertains. Accordingly, the terminologies must be defined based on the following overall description of this specification. Like reference numerals illustrated in the drawings refer to like constituent elements throughout the specification.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween.

Throughout the whole document, the term "comprises or includes" and/or "comprising or including" specify the presence of stated elements or components, but do not preclude the presence or addition of one or more other elements or components, unless mentioned otherwise.

The present disclosure has been accomplished by ascertaining a composition of additives and optimal active ingredients as a result of clinical trials that minimize side effects and increase a lipolysis effect.

A lipolysis composition injection apparatus will be described in detail with reference to example embodiments and the accompanying drawings. It should be understood, however, that there is no intent to limit this disclosure to the particular example embodiments disclosed.

According to an example embodiment, a lipolysis composition injection apparatus may include a lipolysis composition storage, a pump, and at least one nozzle-type needle.

FIG. 1 is a diagram illustrating an apparatus for injecting a lipolysis composition according to an example embodiment. Referring to FIG. 1, a lipolysis composition injection apparatus 100 includes a lipolysis composition storage 110, a pump 120, a nozzle-type needle 130, and a controller 140.

The lipolysis composition storage 110 may include a lipolysis composition or a lipolysis gas.

The lipolysis composition may include at least one lipolytic compound selected from the group consisting of bimatoprost, prostaglandin, latanoprost, traboprost, statin, hyaluronidase, resveratrol, deoxycholic acid, lithocholic acid, isoproterenol, and pentoxypyrin; at least one lipolysis accelerator selected from the group consisting of L-carnitine, carnitine, and levocarnitine chloride; at least one collagen production promotor selected from the group consisting of vitamin C, glycosaminoglycan, and alginic acid; at least one antihistamine selected from the group consisting of olopatadine, azelastine, and phenylaamine; at least one local anesthetic selected from the group consisting of procaine, chloroprocaine, tetracaine, prilocaine, lidocaine, mephibacaine, bupivacaine, lopivacaine, etidocaine, lidocaine hydrochloride, benzocaine, and oxetazin; and a pharmaceutically acceptable carrier.

A lipolytic compound may be a compound decomposing fat, but preferably be at least one selected from the group consisting of bimatoprost, prostaglandin, latanoprost, traboprost, statin, hyaluronidase, resveratrol, deoxycholic acid, lithocholic acid, isoproterenol, and pentoxypyrin.

A lipolysis accelerator may be an accelerator for decomposing fat, but may be at least one selected from the group consisting of L-carnitine, carnitine, and levocarnitine chloride, for example.

A collagen production promotor may be an accelerator for producing collagen, but preferably be at least one selected from the group consisting of vitamin C, glycosaminoglycan, and alginic acid.

An antihistamine is an agent that antagonize an action of histamine. The antihistamine may generally be an agent used for a purpose of preventing or alleviating allergic symptoms, but preferably at least one selected from the group consisting of olopatadine, azelastine, and phenylamine.

A local anesthetic is used for the purpose of relieving pain when injecting injectable compositions. The local anesthetic may generally be an agent used for local anesthetic purposes, but preferably at least one selected from the group consisting of procaine, chloroprocaine, tetracaine, prilocaine, lidocaine, mephibacaine, bupivacaine, lopivacaine, etidocaine, lidocaine hydrochloride, benzocaine, and oxetazin.

A pharmaceutically acceptable carrier may be an oil, a non-aqueous carrier, a diluent, a solvent, or a vehicle used in a composition for parenteral administration, that is, injection or bolus injection. Examples of the oil, the non-aqueous carrier, the diluent, the solvent, or the vehicle may include propylene glycol, polyethylene glycol, vegetable oils (such as olive oil) and injectable organic esters (such as ethyl oleate), or may contain a formulatory agent such as a cosmetic formulatory agent, for example, a preservative, a wetting agent, an emulsifying agent or suspending agent, a stabilizing agent and/or a dispersing agent. The lipolysis composition may be preferably in a form of an injection, and in one aspect, the composition may be an injectable formulation that is mixed with an injectable physiological saline immediately prior to use or may be a liquid formulation dissolved in water for injection.

The lipolysis composition may be administered to, for example, forearm, abdomen, thigh, face, and buttock for removal of local fat. More specifically, the lipolysis composition may be used for a method of removing fat through a lymphatic tube by performing subcutaneous injection at a site having a lot of local fats and massaging the injection site, for example, lipolytic lymph drainage (LLD) treatment.

The lipolysis composition may include 10 volume percent (vol %) to 15 vol % of the lipolytic compound; 5 vol % to 10 vol % of the lipolysis accelerator; 2.5 vol % to 3.0 vol % of the collagen production promotor; 0.03 vol % to 0.04 vol % of the antihistamine; and 0.5 vol % to 0.6 vol % of the local anesthetic. Depending on a body weight, sex, clinical condition, or the like of a subject to be administered, a compounding ratio of components contained in the composition may be changed by a person skill in the art.

When less than 10 vol % of the lipolytic compound is contained, the lipolysis effect may be insufficient. When the lipolytic compound is contained in an amount exceeding 15 vol %, a fat removal may not be evenly performed on a wide area, which may lead to adverse effects such as skin depression, skin deflection, and wrinkling. When less than 5 vol % of the lipolysis accelerator is contained in consideration of a proper maintenance of the lipolytic compound, the lipolysis effect may be insufficient. When the lipolysis accelerator is contained in an amount exceeding 10 vol %, an adverse effect that the lipolysis effect is excessive may occur. When less than 2.5 vol % of the collagen production promotor is contained, a collagen production promoting effect may be insufficient. When the collagen production promotor is contained in an amount exceeding 3.0 vol %, an adverse effect that collagen is excessively produced may occur. When less than 0.03 vol % of the antihistamine is contained, an allergy preventing effect may be insufficient. When the antihistamine is contained in an amount exceeding 0.04 vol %, an adverse effect due to the antihistamine may occur. When less than 0.5 vol % of the local anesthetic is contained, an effect of anesthesia may be insufficient. When the local anesthetic is contained in an amount exceeding 0.6 vol %, a time required for wearing off the anesthesia may be prolonged, which may result in an inconvenience in daily life after the treatment.

The hyaluronidase of the lipolytic compound may be in a most effective unit for fat decomposition, but preferably 600 international unit (IU) to 900 IU may be used. When a unit of the hyaluronidase includes less than 600 IU, the lipolysis effect may be insufficient and a number of times of injection may increase because an interval between injections needs to be reduced. When the hyaluronidase is contained in excess of 900 IU, the fat composition may be excessively performed, which may lead to a skin depression that causes a ruggedness of the skin. Also, in the unit range, when an injection of 1 cubic centimeter (cc) dose was injected in units of 600 IU, a diffusion range of the effective component was confirmed to be 1 to 2.5 cm. Accordingly, the injections may be performed at intervals of 1 cm to 2.5 cm, so that the number of times of injection is reduced and the fat decomposition is evenly performed.

The lipolysis gas may include at least one gas of carbon dioxide, oxygen, and hydrogen. In addition, the lipolysis gas may also include all other gases used for fat decomposition.

The lipolysis composition injection apparatus may sequentially inject the lipolysis gas and the lipolysis composition into the skin. By employing a treatment method that separates layers by inserting the lipolysis gas into a skin layer and injects the lipolysis composition while a space is secured, the lipolysis composition injection apparatus may effectively inject medicine between the skin layer and a subcutaneous layer and perform stable and efficient lipolysis treatment with increased accuracy.

The lipolysis composition storage 110 may include a plurality of lipolysis composition storages 110, each storing the lipolysis gas or the lipolysis composition.

The pump 120 may periodically supply the lipolysis composition to the nozzle-type needle 130.

The nozzle-type needle 130 may be provided to inject the lipolysis gas or the lipolysis composition stored in the lipolysis composition storage 110 into a site requiring the lipolysis treatment, for example, thigh, calf, buttock, and face.

The controller 140 may control an injection volume, a number of times of injection, an injection time, an injection depth, and the like based on a site to into which the lipolysis composition is to be injected.

The lipolysis composition may be jetted at a high pressure to a subcutaneous fat layer through the nozzle-type needle 130.

The lipolysis composition may be periodically jetted at a high pressure to the subcutaneous fat layer through the nozzle-tip needle in response to the periodical supply of the pump. The periodical supply of the lipolysis composition may minimize an impact or stimulation to subcutaneous fat.

Through the periodical high-pressure jet, an oscillation may be applied to the subcutaneous fat layer. A continuity may be achieved in the periodical high-pressure jet due to the periodical high-pressure jet, which may maximize a lipolysis efficiency in the subcutaneous fat.

The oscillation may be a repetitive oscillation of 10 hertz (Hz) to 1000 Hz. This range of oscillation may lead to an appropriate balance between a lipolysis composition delivery range and a permeability to a subcutaneous fat layer.

The high-pressure jet may be performed at a pressure of 50 pounds per square inch (psi) to 1000 psi. When the injection is performed at a pressure of less than 50 psi, the pressure may not sufficient to result in fat decomposition. When the injection is performed at a pressure above 1000 psi, the pressure may result in excessive shock or irritation to a periphery.

The lipolysis composition may be supplied at a volume of 300 milliliters per minute (ml/min). Anon-invasive complex fat decomposition may be performed by administering the lipolysis composition at a dose within the above-mentioned range together with the oscillation, so that a fat decomposition efficiency and a removal efficiency of a fat accumulation site in a body are increased.

The nozzle-type needle 130 may include four to eight nozzle-type needles. The administration may be simultaneously performed by at least four injection points whereby the treatment time is reduced.

The nozzle-type needles 130 may be positioned at an interval of 10 centimeters (cm) to 20 cm and inserted into the subcutaneous fat layer. When an interval between nozzle-type needle points is less than 10 cm, a number of times of injection may increase. Also, an effective component of the composition may redundantly act on the skin so that the fat decomposition is performed excessively in a portion of the skin, which may lead to a phenomenon that the skin becomes rugged at dense intervals. When an interval between nozzle-type needle points is greater than 20 cm, the effective component of the composition may not function uniformly so that a fat removal is not evenly performed on a wide area.

The lipolysis composition may be administered at a depth that optimizes the lipolysis effect depending on an administration site of the subject, by may preferably be administered at a depth of 4 millimeters (mm) to 6 mm from a surface of the skin.

Figure 2:
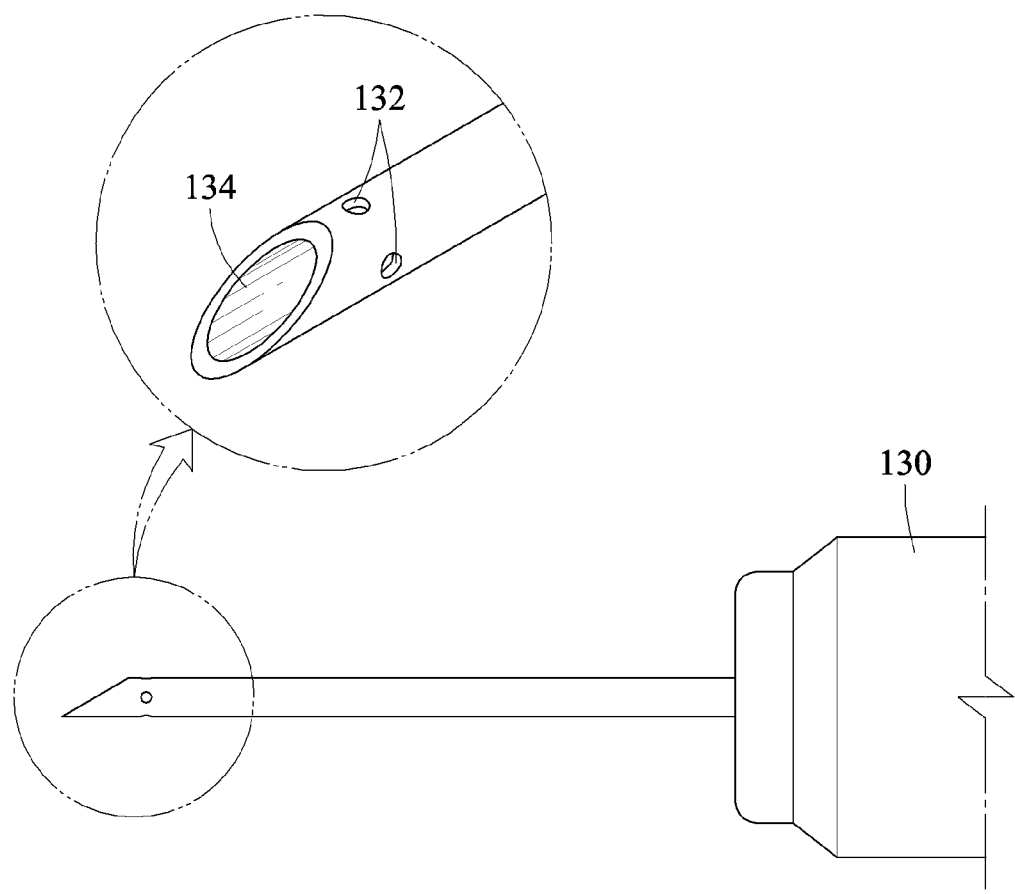
FIG. 2 is a diagram illustrating a nozzle-type needle according to an example embodiment.

FIG. 2 is a diagram illustrating a nozzle-type needle according to an example embodiment. Referring to FIG. 2, the nozzle-type needle 130 may include a horizontal jet hole 132 and a central jet hole 134 at an end of the nozzle-type needle.

Figure 3:
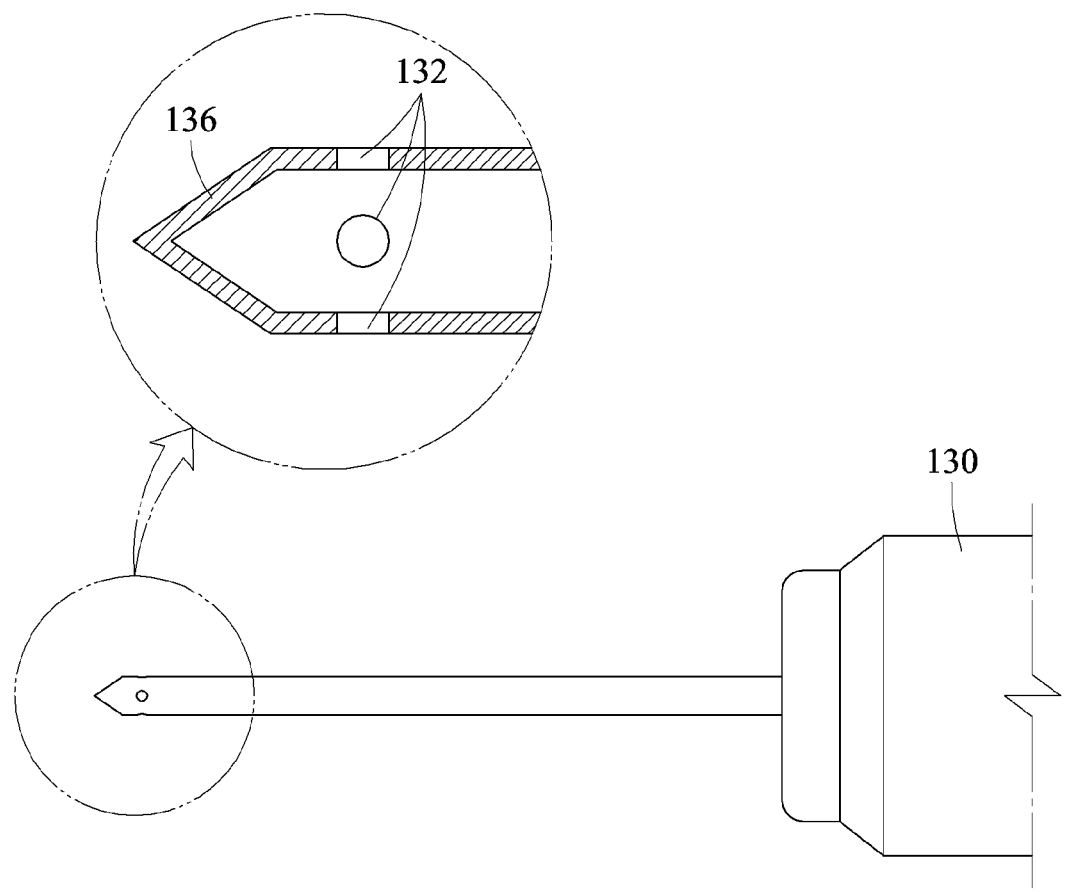
FIG. 3 is a diagram illustrating a nozzle-type needle according to an example embodiment.

FIG. 3 is a diagram illustrating a nozzle-type needle according to an example embodiment. Referring to FIG. 3, a longitudinal end 136 of the nozzle-type needle 130 may be blocked.

Figure 4:
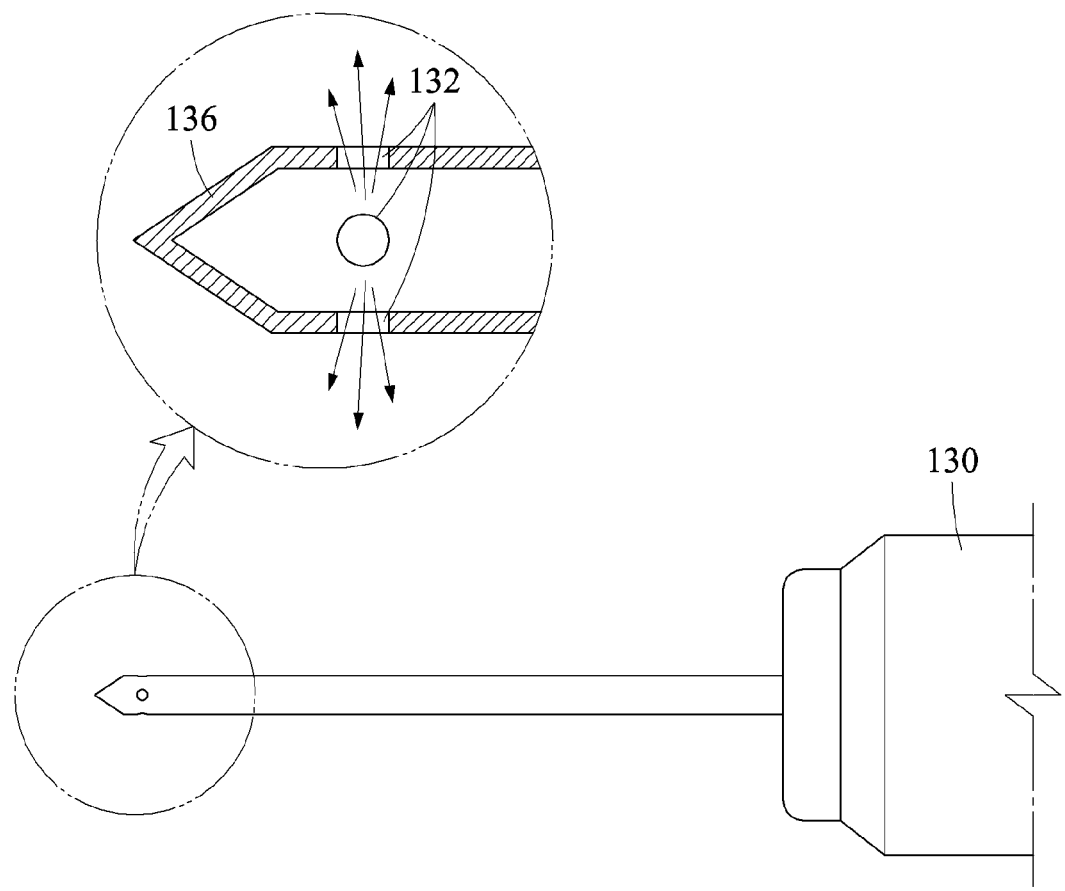
FIG. 4 is a diagram illustrating a nozzle-type needle jetting a lipolysis composition through a horizontal jet hole according to an example embodiment.

FIG. 4 is a diagram illustrating a nozzle-type needle jetting a lipolysis composition through a horizontal jet hole according to an example embodiment. Referring to FIG. 4, a jet of a lipolysis composition performed through a horizontal jet hole of the nozzle-type needle 130 may include a radial spraying jet.

Figure 5:
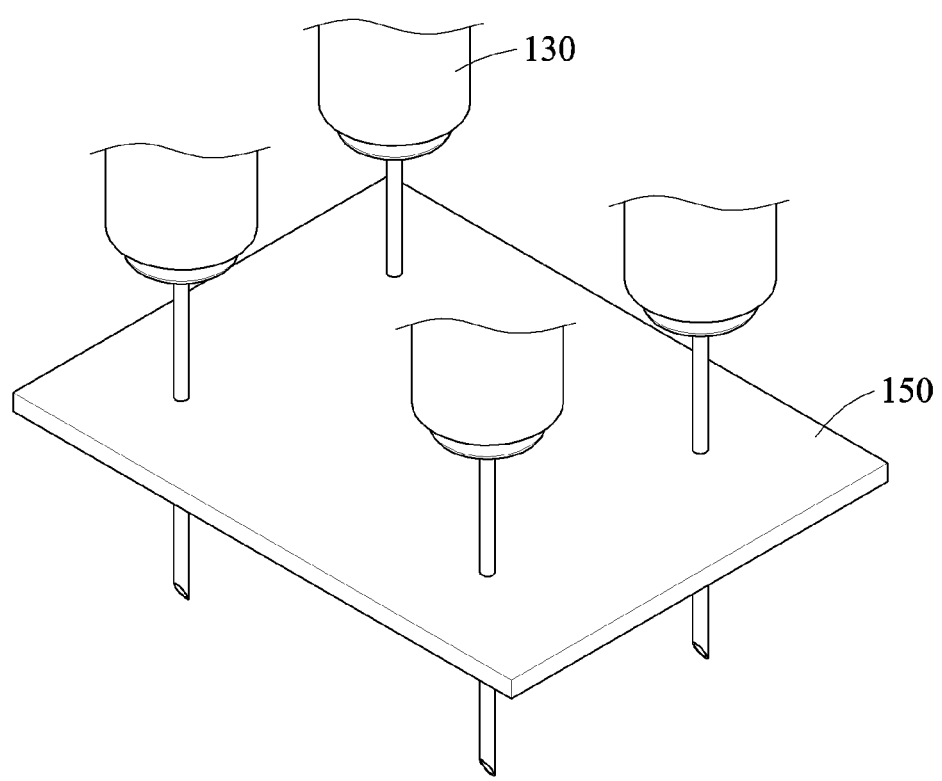
FIG. 5 is a diagram illustrating a nozzle-type needle penetrating a flexible patch plate according to an example embodiment.

FIG. 5 is a diagram illustrating a nozzle-type needle penetrating a flexible patch plate according to an example embodiment. Referring to FIG. 5, the nozzle-type needle 130 may penetrate a flexible patch plate 150.

The nozzle-type needle may be four or more needles and provided at an interval of 10 cm to 20 cm to penetrate the flexible patch plate. A length by which the nozzle-type needle penetrates the flexible patch plate may be adjustable in a range of 1 cm to 5 cm. The needle penetrating the flexible patch plate may be attached to a lipolysis target site in a form of a patch and delivered to the target site. By applying the form of the patch, the administration may be simultaneously performed using a plurality of injection points positioned at preset intervals, which may reduce the treatment time.

Hereinafter, the present disclosure will be described in detail with reference to examples.

However, the following examples are illustrative only, and do not limit the scope of the present disclosure.

Example 1

1. Lipolysis Composition Preparation and Treatment

A lipolysis composition for injection was prepared as shown in Table below.

TABLE 1

| Component | Lipolytic compound | Lipolysis accelerator | Collagen production promotor | Antihistamine | Local anesthetic | Carrier |
|---|---|---|---|---|---|---|
| Example 1 | Hyaluronidase 700 IU | Carnitine 10% (v/v) | Vitamin C 3.0% (v/v) | Phenylamine 0.04% (v/v) | Lidocaine 0.6% (v/v) | Physiological saline remaining |
| Example 2 | Resveratrol 15% (v/v) | | | | | |
| Example 3 | Statin 15% (v/v) | | | | | |

A lipolysis composition for injection was prepared by mixing hyaluronidase (Daehan New Pharm Co., Ltd.), carnitine (MEDEME CO., LTD.), vitamin C (DAOOM), phenylamine (YUHAN CORPORATION), lidocaine (DAI HAN PHARM. CO., LTD.), resveratrol (Solgar Inc), and statin (United Interpharm) in the above amounts.

2. Lipolysis Effect of Lipolysis Composition

A treatment for examining a lipolysis effect was performed by putting lipolysis compositions of Examples 1 through 3 into the lipolysis composition storage of the lipolysis composition injection apparatus. Administration was performed on abdomen of ten male and female patients over 20 years of age with abdominal obesity above BMI 25 or more at intervals of 2 cm. An average of the results is shown in table 2 below.

TABLE 2

| Composition | Difference in waist circumference after administration | Difference in waist circumference after 1 month | Skin depression phenomenon |
|---|---|---|---|
| Example 1 | −5.6 ± 0.4 | −0.6 ± 0.4 | X |
| Example 2 | −4.3 ± 0.2 | +0.2 ± 0.1 | X |
| Example 3 | −4.0 ± 0.3 | +0.4 ± 0.2 | X |

As a statistical analysis and validation method, an SPSS statistical package were used to obtain a distribution of measured values. A paired t-test were used to examine an effect of waist circumference reduction for each test injection. A validity interval for reliability were determined to be within 95%. The lipolysis compositions of Examples 1 through 3 were put into the lipolysis composition storage of the lipolysis composition injection apparatus to observe the lipolysis effect. As a result, a remarkable decrease in waist circumference was exhibited, skin depression did not occur, and weight cycling was not found after one month.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An assembly for injecting a lipolysis composition, the assembly comprising:
    a flexible patch plate; and
    an apparatus comprising:
        a lipolysis composition storage;
        a pump; and
        at least four nozzle-type needles, wherein the at least four nozzle-type needles are spaced apart relative to one another by between 10 cm to 20 cm to define a matrix, such that the at least four nozzle-type needles simultaneously penetrate the flexible patch plate at preset intervals based upon the matrix.

2. The assembly of claim 1, wherein the pump is configured to periodically supply the lipolysis composition to the nozzle-type needle.

3. The assembly of claim 1, wherein the lipolysis composition is jetted at a pressure into a subcutaneous fat layer through the nozzle-type needle.

4. The assembly of claim 1, wherein a periodical pressure jet of the lipolysis composition is supplied to a subcutaneous fat layer through the at least one nozzle-type needle in response to a periodical supply of the pump.

5. The assembly of claim 4, wherein an oscillation is applied to the subcutaneous fat layer through the periodical pressure jet.

6. The assembly of claim 5, wherein the oscillation is a repetitive oscillation of 10 hertz (Hz) to 1000 Hz.

7. The assembly of claim 4, wherein the pressure jet is provided at a pressure of 50 pounds per square inch (psi) to 1000 psi.

8. The assembly of claim 4, wherein the lipolysis composition is supplied at a volume of 300 milliliters per minute (ml/min).

9. The assembly of claim 1, wherein a longitudinal end of the nozzle-type needle is blocked.

10. The assembly of claim 1, wherein:
    the at least one nozzle-type needle comprises four or more needles each provided at an interval of 10 cm to 20 cm to penetrate a flexible patch plate, and
    a length by which each of the four or more needles penetrates the flexible patch plate is adjustable in a range of 1 cm to 5 cm.

11. The assembly of claim 1, wherein the lipolysis composition is administered at a depth of 4 millimeters (mm) to 6 mm from a surface of skin.

* * * * *